United States Patent
Pedicini et al.

(10) Patent No.: US 12,171,518 B2
(45) Date of Patent: Dec. 24, 2024

(54) INTERMEDIARIES FOR ROBOTS AND ROBOTIC END-EFFECTORS FOR ORTHOPEDIC SURGERY

(71) Applicant: Fidelis Partners, LLC, Cheyenne, WY (US)

(72) Inventors: Christopher Pedicini, Franklin, TN (US); Joshua Pedicini, Franklin, TN (US)

(73) Assignee: FIDELIS PARTNERS, LLC, Cheyenne, WY (US)

(*) Notice: Subject to any disclaimer, the term of this patent is extended or adjusted under 35 U.S.C. 154(b) by 441 days.

(21) Appl. No.: 17/151,827

(22) Filed: Jan. 19, 2021

(65) Prior Publication Data
US 2022/0008151 A1    Jan. 13, 2022

Related U.S. Application Data

(60) Provisional application No. 63/042,069, filed on Jun. 22, 2020.

(51) Int. Cl.
*A61B 34/00* (2016.01)
*A61B 17/00* (2006.01)
*A61B 17/56* (2006.01)
*A61B 34/30* (2016.01)
*B25J 19/00* (2006.01)

(52) U.S. Cl.
CPC .............. *A61B 34/70* (2016.02); *A61B 17/56* (2013.01); *A61B 34/30* (2016.02); *B25J 19/0091* (2013.01); *A61B 2017/00477* (2013.01)

(58) Field of Classification Search
CPC .................. A61B 34/70; A61B 34/30; A61B 2017/00477; A61B 17/56; B25J 19/0091
See application file for complete search history.

(56) References Cited

U.S. PATENT DOCUMENTS

| | | | |
|---|---|---|---|
| 2012/0235606 A1* | 9/2012 | Takeuchi | H02K 7/116 318/371 |
| 2018/0055554 A1* | 3/2018 | Pedicini | A61B 90/30 |
| 2019/0059932 A1* | 2/2019 | Isosaki | A61B 18/1445 |
| 2019/0183555 A1* | 6/2019 | Pedicini | B25D 17/005 |
| 2022/0233225 A1* | 7/2022 | Pedicini | A61B 17/92 |

OTHER PUBLICATIONS

Chinese Patent No. CN 110017344 to Wang et al published on Jul. 16, 2019.*
German Patent No. DE 102013002818 to Gombert et al published on Aug. 21, 2014.*

* cited by examiner

*Primary Examiner* — Pamela Rodriguez
(74) *Attorney, Agent, or Firm* — XSENSUS LLP

(57) ABSTRACT

Intermediaries for a robot and robotic end effector for orthopedic surgery operatively couple a surgical robot to an end effector of such a robot. The intermediaries therefor comprise means to absorb and/or counteract reactionary forces from the end effector (which end effector may, as an example, be a surgical tool) and to reduce forces that would otherwise be imparted on the robot. An intermediary comprises a sleeve of shock-absorbing material that couples the robot and end effector. Another intermediary comprises an isolation connector that provides for an indirect coupling between the robot and the end effector and includes an absorption means for absorption or dispersion of reactionary forces from the end effector.

6 Claims, 2 Drawing Sheets

$$F_1 \Delta t_1 = F_2 \Delta t_2 \quad \text{— As an Example}$$

$$(120)(0036) = F_2 (.072)$$

$$F_2 = 6\text{lbs}$$

INTERMEDIARIES FOR ROBOTS AND ROBOTIC END-EFFECTORS FOR ORTHOPEDIC SURGERY

CROSS-REFERENCE TO RELATED APPLICATIONS

The present disclosure claims priority under 35 U.S.C. § 119 on U.S. Provisional Application Ser. No. 63/042,069 filed on Jun. 22, 2020, the disclosure of which is incorporated by reference.

FIELD OF THE DISCLOSURE

The present disclosure relates to intermediaries for surgical robots and robotic end effectors and more specifically, to the enablement of surgical robots to handle and manipulate end effectors (such as surgical power tools) with minimal external force imparted upon such robots.

BACKGROUND OF THE DISCLOSURE

The current direction of surgery is towards using robot assistance in the surgery process. In this regard, an end effector of the robot may be used by a robot, i.e., to perform a surgical procedure. The end effector is, in an embodiment, a device, tool, or manipulator at an end of the robot that is capable of engaging and interacting with a surgical site. The end effector is directed by the robot to perform surgical actions. In the field of robotic surgery, the end effector often comprises a surgical tool.

To date, robotic automation in surgery has worked well in laproscopic procedures and surgeries with low energy requirements, however, in the orthopedic environment where large forces and energies are routine, the adoption of the robot has been hindered. In such an environment and in the field of orthopedic surgery, larger energy requirements have necessitated a different approach (such as machining) due to the inability of surgical robots to handle the magnitude of reactionary forces that result from typical large bone surgical tools (such as saws or reamers).

An exemplary robot that is used in large bone surgeries is Stryker Corporation's MAKO product. The MAKO has three purposes: enhanced planning, dynamic joint balancing, and robotic-arm assisted bone preparation.

As part of its operation, such a robot must have the bone geometry of the surgical site identified in order to accurately navigate, guide, and manipulate its end effector through the surgical site. Such identification of bone geometry is commonly referred to as registration. Existing surgical power tools produce a significant amount of torque (such as in the case of a surgical reamer) or shock (such as in the case of a surgical impacting tool) when used in orthopedic surgery. This torque or shock can not only cause the robot to lose its registration but it can also damage the robot's highly intricate machinery and components.

Linear impactors are used in hip and hip replacement surgeries such as when seating the acetabular cup of a prosthetic hip or in broaching the femoral canal. These impactors can be pneumatic or electric, for example, and have a significant recoil force associated with impact. Testing has shown that this recoil can damage the robot arm, which damage understandably can be detrimental to the operation of the robot and to the surgery process itself.

The navigation capability is arguably the most important feature of orthopedic robotics. For a successful surgery, the robot must hold the tool (or instrument) in the correct orientation and alignment with respect to the bone. If the surgical instrument is allowed to move off the stereotactic boundary then the surgery can suffer from any of a number of drawbacks, including injury to soft tissue if the instrument is still powered. Currently-available linear and rotary impactors can generate large destabilizing forces (recoil or impulse, as measured by Force*time or torque*time, for example). These forces impede the ability of the robotic end effector to be or remain precisely positioned during surgery, and in a severe case damage the robot or cause it to shut down There are at least two problems with simply placing a surgical power tool in a robot end effector, which problems are related to either shock or torque. One, the shock or torque imparted by the tool can severely damage the robot. Two, the shock or torque will cause the end effector to shift physically, causing loss of registration by the robot. Currently, there is not a means for enabling a surgical power tool to be completely operated by a robot for at least the reason that current solutions require stabilizing the arm and/or providing force by a surgeon.

Accordingly, a need exists for intermediaries for a robotic end effector that provide for complete operation of a surgical tool by a robot. A solution to deficiencies of the prior art may come in the form of a reactive shock absorbing sleeve or other absorption means to reduce reactionary forces (e.g. torque and/or shock) of end effectors (such as surgical power tools) on robots.

SUMMARY OF THE DISCLOSURE

In view of the foregoing disadvantages inherent in the prior art, the purpose of the present disclosure is to provide a solution to the high reactionary forces (torque, shock, recoil, and the like) that occur from orthopedic surgical tools. These solutions work to reduce the reactionary forces upon a surgical robot and allow a such a surgical robot to retain registration and/or perform surgery with minimal outside assistance.

DESCRIPTION OF THE DRAWINGS

The advantages and features of the present disclosure will become better understood with reference to the following detailed description and claims taken in conjunction with the accompanying drawings, wherein like elements are identified with like symbols, in which:

DETAILED DESCRIPTION OF THE DISCLOSURE

The exemplary embodiments described herein detail for illustrative purposes are subject to many variations in structure and design. It should be emphasized, however, that the present disclosure is not limited to a particular surgical tool, robot, robotic end effector, or any intermediaries as shown and described. That is, it is understood that various omissions and substitutions of equivalents are contemplated as circumstances may suggest or render expedient, but these are intended to cover the application or implementation without departing from the spirit or scope of the claims of the present disclosure. The terms "first," "second," and the like, herein do not denote any order, quantity, or importance, but rather are used to distinguish one element from another, and the terms "a" and "an" herein do not denote a limitation of quantity, but rather denote the presence of at least one of the referenced item.

The present disclosure provides for intermediaries for a robot and robotic end effector for orthopedic surgery. An intermediary in this context may be understood to be a component of or attachment B to a surgical robot A that operatively couples the robot A to an end effector C. The intermediaries therefor comprise means to absorb and/or counteract (also referred to herein as "absorption means") reactionary forces from the end effector (such as a surgical tool) and to reduce forces that would otherwise be imparted on a robot. As used herein, "reactionary force" may include linear or rotary shock or impulse, and/or force reflected back to the robot, for example.

That is, existing configurations have the robot physically and otherwise directly attached to the end effector, such that the reactionary force from an end effector is consequently imparted onto the surgical robot. As disclosed herein the intermediary or intermediaries obviates this direct attachment between the surgical robot and the end effector, thus preventing the direct impartation of reactionary forces on the surgical robot and, in fact, significantly reducing if not entirely eliminating such reactionary forces from acting on the surgical robot. For purposes of the present disclosure, it will be apparent that the end effector may be a surgical tool, for example.

Figure 1:
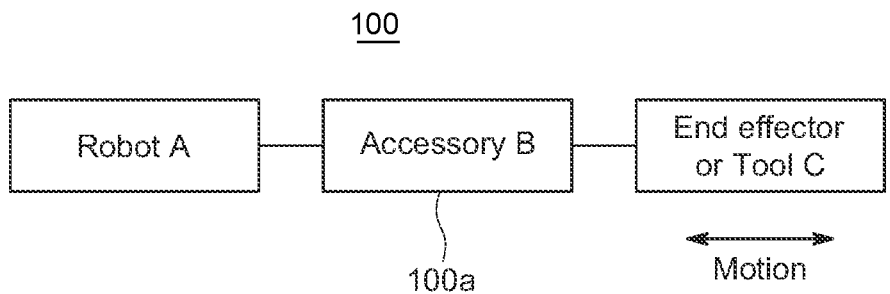
FIG. 1 shows a force isolating sleeve that absorbs reactionary forces that would otherwise be imparted onto a robot in a direct-connect surgical implement in accordance with the disclosure herein.

In an embodiment, and as shown in FIG. 1, the absorption means 100 comprise a shock absorbing member or means 100a for absorbing force that emanates from an end effector C, for example.

Figure 2:
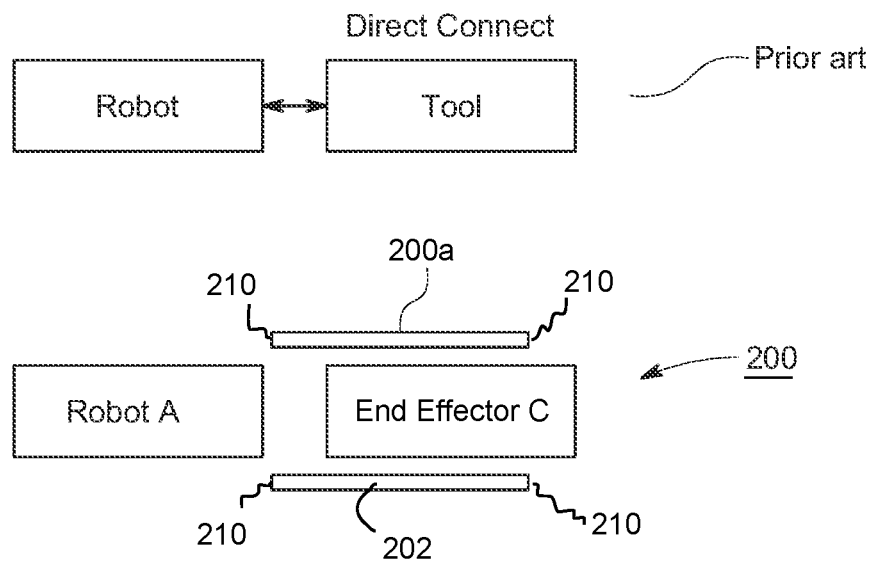
FIG. 2 shows a prior-art direct connection between a robot and a surgical tool as well as, in accordance with an exemplary embodiment of the present disclosure, an isolation connection between a robot and surgical tool.

In an embodiment and as shown in FIG. 2, the intermediary 200 comprises an isolation (or isolated) connector 200a between a robot A and an end effector C for reducing the force of the end effector on the robot A. This isolation connector 200a is preferably configured (e.g., tuned) with respect to the end effector such that the isolation connector 200a prevents registration loss during surgery. In an embodiment, the movement of the isolation connector 200a and/or end effector C can be incorporated into the robot A to allow for self-compensation and minimize loss of registration. The isolation connector is configured to reduce or eliminate action of reactionary forces on the robot. In an embodiment, isolation connector 200a comprises a sleeve of shock absorbent material. In another embodiment, isolation connector comprises a dashpot/spring configuration.

In an embodiment, and as shown in FIG. 1, the shock-absorbing member 100a comprises a sleeve that couples a robot A and robot end-effector C. In said embodiment, the sleeve 100a is capable of receiving at least a portion of the robot A and at least a portion of the robotic end-effector C. Said sleeve 100a may be made from a material (such as Sorbothane) that may absorb reactionary forces from a surgical tool. In an embodiment, the aforementioned sleeve 100a fully absorbs the tool's reactionary force (such that no such force is transmitted to robot A) and recovers to its initial position or configuration in a set amount of time (in the case of impacting) before the next impact by the tool. The sleeve 100a may be removably attached to the robotic end effector C and/or robot A for sterilization and reuse after a procedure. In an embodiment the sleeve 100a is a disposable and therefore single use only.

Figures 3, 4:
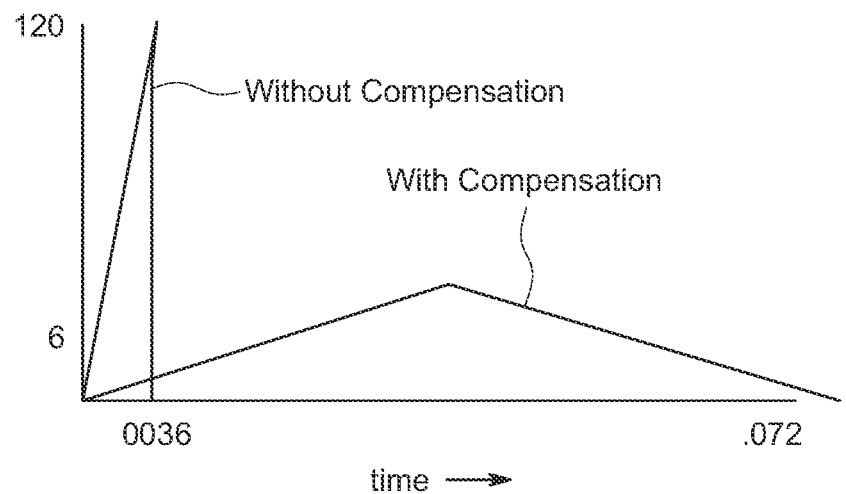
FIG. 3 shows a plot of force vs time (impulse plot) that exemplifies reactionary force reduction in accordance with an exemplary embodiment of the present disclosure.
FIG. 4 shows a sample calculation of reactionary force reduction by expanding the time period over which that force is applied in accordance with an exemplary embodiment of the present disclosure.

In an embodiment, the reactionary force that is seen from the impact by end effector C may be reduced by extending the time period (as shown in FIGS. 3 and 4) over which the thrown member impacts a surface. This occurs due to the law of conservation of momentum ($m_1 v_1 = m_2 v_2$) which can also be written in terms of impulse as $F_1 \Delta t_1 = F_2 \Delta t_2$ (where F is force and $\Delta t$ is the time period over which that force occurs). The time period ($\Delta t$) can be extended by using a viscoelastic material such as Sorbothane, such as in the form of a sleeve 100a that surrounds the robot A and/or robotic end effector C.

In an embodiment, isolation connector 200a that connects a robotic end-effector C (such as a surgical tool) and a robot A provides for an indirect but still secure operative coupling between the robot A and the end effector C. The isolation connector 200a also provides an absorption means 202 for absorption or dispersion of reactionary forces from the end effector C. In an embodiment, absorption means 202 of the isolation connector 200a comprises a shock absorbing material such as urethane (including but not necessarily limited to sorbothane and viscose), for example. In a still further embodiment the absorption means 202 of isolation connector 200a comprises dampening materials, and in a further embodiment, said dampening materials have a coefficient of restitution (COR) of less than 0.5. In an embodiment, isolation connector 200a comprises a sleeve of shock-absorbing material.

In another embodiment, the isolation connector 200a comprises a plurality of connections 210 between and amongst the end effector C and surgical robot A such that there is no direct physical connection between the robot A and end effector C and the reactionary force of the end effector C upon the robot A is consequently minimized.

The present disclosure offers the following advantages: reduction of reactionary forces from a surgical tool upon a robot, which force reduction results in less wear and tear on the components of the robot as well as improved performance by the robot due to the reduction in the instances of loss of registration of the robot upon the surgical site.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the disclosure and various embodiments with various modifications as are suited to the particular use contemplated.

What is claimed is:

1. An intermediary for at least one of an orthopedic surgery robot and robot end-effector, the intermediary comprising an absorption means, said absorption means capable of receiving a force imparted by the end-effector and capable of reducing the impartation of the force from the end-effector upon the robot, wherein a time duration of the end-effector's force impartation is extended to reduce the force imparted on the robot.

2. The intermediary of claim 1, wherein the absorption means comprises a sleeve of shock-absorbing material that is disposed on at least part of the end-effector.

3. The intermediary of claim 1, wherein a peak force imparted by the end-effector is reduced by at least 50%.

4. An intermediary for a robot end-effector for orthopedic surgery, said intermediary comprising an isolation connector, said isolation connector capable of indirectly coupling with an orthopedic surgery robot and robot end-effector, said isolation connector capable of absorbing a force of the end-effector that would otherwise be imparted on the robot, wherein said connector extends the time duration over which a force is imparted.

5. The isolation connector of claim 4, wherein said connector comprises a plurality of couplings with at least one of the robot and end-effector.

6. The isolation connector of claim 4, said connector comprising an absorbing material that is disposed on at least a portion of at least one of the robot and end-effector.

\* \* \* \* \*